(12) United States Patent
Knoefel

(10) Patent No.: US 9,603,572 B2
(45) Date of Patent: Mar. 28, 2017

(54) ANALYSIS DEVICE WITH USER-FRIENDLY MENU CONTROLS

(75) Inventor: Anja Knoefel, Dresden (DE)

(73) Assignee: Roche Diabetes Care, Inc., Indianapolis, IN (US)

(*) Notice: Subject to any disclaimer, the term of this patent is extended or adjusted under 35 U.S.C. 154(b) by 257 days.

(21) Appl. No.: 13/088,194

(22) Filed: Apr. 15, 2011

(65) Prior Publication Data

US 2011/0282174 A1 Nov. 17, 2011

Related U.S. Application Data

(63) Continuation of application No. PCT/EP2009/063394, filed on Oct. 14, 2009.

(30) Foreign Application Priority Data

Oct. 16, 2008 (EP) .................................. 08166803

(51) Int. Cl.

| | |
|---|---|
| *G01N 33/00* | (2006.01) |
| *A61B 5/00* | (2006.01) |
| *A61B 5/145* | (2006.01) |
| *G01N 33/487* | (2006.01) |
| *A61B 5/15* | (2006.01) |
| *A61B 5/157* | (2006.01) |

(Continued)

(52) U.S. Cl.

CPC ........ *A61B 5/7435* (2013.01); *A61B 5/14532* (2013.01); *A61B 5/14546* (2013.01); *A61B 5/157* (2013.01); *A61B 5/150022* (2013.01); *A61B 5/150175* (2013.01); *A61B 5/150259* (2013.01); *A61B 5/150305* (2013.01); *A61B 5/150358* (2013.01); *A61B 5/7475* (2013.01); *G01N 33/48785* (2013.01); *A61B 5/15186* (2013.01); *A61B 5/150412* (2013.01); *A61B 5/150503* (2013.01); *G06F 19/3406* (2013.01)

(58) Field of Classification Search
None
See application file for complete search history.

(56) References Cited

U.S. PATENT DOCUMENTS

| | | |
|---|---|---|
| 6,585,698 B1 | 7/2003 | Packman et al. |
| 2007/0093786 A1 | 4/2007 | Goldsmith et al. |

(Continued)

FOREIGN PATENT DOCUMENTS

| | | |
|---|---|---|
| EP | 1338295 | 8/2003 |
| WO | WO 2008/154312 | 12/2008 |

*Primary Examiner* — Sam P Siefke
(74) *Attorney, Agent, or Firm* — Harness, Dickey

(57) ABSTRACT

An analysis device is proposed for detecting an analyte in a liquid sample, in particular for detecting glucose in a bodily fluid. The analysis device comprises at least one control element, which is configured to provide a function menu with at least two menu items. The analysis device further comprises at least one adjustable selector element, in particular a mechanically adjustable selector element, which can be adjusted by a user to at least two different selection positions. The selector element is configured to remain in the adjusted selection position after being adjusted. The control element is configured to select a menu item corresponding to the adjusted selection position. The analysis device further comprises at least one operating element. At least one parameter in the selected menu item can be influenced by the user via the operating element.

19 Claims, 5 Drawing Sheets

(51) Int. Cl.
*G06F 19/00* (2011.01)
*A61B 5/151* (2006.01)

(56) References Cited

U.S. PATENT DOCUMENTS

| | | |
|---|---|---|
| 2007/0179358 A1 | 8/2007 | Perez |
| 2008/0114299 A1 | 5/2008 | Damgaard-Sorensen et al. |
| 2008/0171922 A1 | 7/2008 | Teller et al. |
| 2008/0262469 A1* | 10/2008 | Brister et al. ............... 604/504 |

* cited by examiner

ANALYSIS DEVICE WITH USER-FRIENDLY MENU CONTROLS

CROSS-REFERENCE TO RELATED APPLICATIONS

This application is a continuation of International Patent Application No. PCT/EP2009/063394, filed on Oct. 14, 2009, which claims the benefit and priority of European Patent Application No. 08166803.0, filed Oct. 16, 2008. The entire disclosures of the above applications are incorporated herein by reference.

BACKGROUND

The invention relates to an analysis device for detecting an analyte in a liquid sample. Such analysis devices are used in various areas of natural science, medicine and technology in order to detect various types of analytes in various samples. The present application focuses on uses in the field of medical technology for detection of one or more analytes in a bodily fluid; for example, blood, interstitial fluid or urine. These analytes can, for example, comprise metabolites. Examples of such analytes are glucose, lactate, cholesterol or similar substances and/or properties of the sample; for example, coagulation. The invention, however, is not limited to said uses.

Analysis devices are used in various areas of natural science, medicine and technology. Without limiting possible further embodiments of the analysis device according to the invention, reference is mainly made herein to analysis devices that are used for detecting blood glucose in particular analysis devices designed as hand-held devices.

SUMMARY

In the field of health care, diagnosis or therapy, it is in many cases necessary to determine physical functions quickly and reliably. A typical example is the diagnosis and treatment of blood glucose disorders such as type I or type II diabetes. Diabetics generally have to measure their blood glucose concentration at least once a day, or typically up to seven times a day, and must do so quickly and reliably. So as not to restrict the diabetic's daily routine any more than is necessary, analysis devices were therefore developed that are portable and that allow quick and reliable qualitative and/or quantitative detection of the at least one analyte, in particular blood glucose, even during leisure time, at the workplace or at other locations. Within the context of the present invention, reference can also be made to known analysis devices of this kind.

The qualitative and/or quantitative detection of the at least one analyte takes place, for example, optically and/or electrochemically. For example, test elements can be used that comprise at least one detection material which, upon contact with the analyte to be detected, specifically and measurably changes at least one physical and/or chemical property. For example, analytes such as blood glucose can be detected optically and/or electrochemically in this way. The test elements can be designed in a wide variety of ways as individual test elements and/or as test elements for multiple uses. For example, individual test strips, multiple test strips, test tapes with one or more test panels, foldable test elements, test tubes, test disks with one or more test panels or other embodiments are known. All types of known test elements can be used in principle in the context of the present invention.

Analysis devices generally have at least one control element which can control one function, several functions or all the functions of the analysis device. This control element can, for example, control the qualitative and/or quantitative detection of the at least one analyte. For this purpose, for example, measurement signals can be evaluated, measured data stored, measured data evaluated, measured data managed, measured data transmitted to other devices, measured data presented to a user optically and/or acoustically and/or haptically, or similar functions performed. For example, such control elements can comprise one or more data processors and, if appropriate, one or more non-volatile and/or volatile data memories.

Analysis devices and/or the control elements thereof generally have a menu control which, for example, can be completely or partially implemented by suitable software. A menu control of this kind can, for example, allow a user to control and/or use the analysis device. For example, the menu control can permit access to and/or control of the data memory and/or can permit evaluation and/or presentation of measured data.

The configuration of the menu control involves considerable technical demands. Thus, blood glucose meters in particular are provided for a wide range of users, possibly including children or elderly patients. However, analysis devices, which generally have to be produced under considerable cost constraints and have to be as compact as possible, usually have only two or three operating elements available to the user for the purpose of menu control. Because of the small number of operating elements, a user often has to laboriously work through a menu structure of the menu control in order to be able to select and/or control specific functions in the analysis device. However, for children or elderly patients in particular, awkward menu control of this kind in some cases causes considerable problems since, for example, many patients in said target groups are unaccustomed to working with menu options merely shown on a display and to selecting one or more of these functions.

Another requirement of such menu controls is that the indicator elements, such as displays, of such analysis devices have to be very flexible in terms of the display options in order to show the menu options of the menu control in an intelligible way. Thus, the user should be able to fully work out the meaning of the displayed information without having to consult a user manual. In particular, the functions and/or parameters listed in a defined menu level should be clear to the user without the need for additional information and/or background knowledge.

However, this comprehensible display of information, which can be of widely different kinds and can vary, generally requires complicated indicator elements. For example, simple segmented displays, for example the known seven-segment displays, can often be used only to a limited extent, if at all, in analysis devices of the type described, since the flexibility of such displays and/or the nature of the information that can be shown by means of these displays is extremely limited. However, these segmented displays are in many cases actually desirable and are preferred to other types of displays, for example pixelated displays. Such displays are generally easier to read in terms of their reading angle and/or in terms of their clarity, which is a considerable advantage in particular for elderly patients. A further aspect is that, in contrast to pixelated displays, segmented displays require considerably simpler electronic control and generally also have a lower energy requirement and are more compact. Cost aspects also play an important role, since analysis devices for private use are generally produced under considerable price constraints.

From other areas of medical technology, devices are known which likewise require operation by a user. For example, U.S. Pat. No. 6,585,698 B1 describes a medication pen with a housing and an actuator for setting and making available a dose of medicament. A processor is coupled to the actuator in order to determine a value that corresponds to a dose set by the actuator. The information made available by the processor is shown on a display. The actuator in this case has two states. In a first state, the actuator couples to a drive mechanism in order to make available the medication. In a second state, the actuator is uncoupled from the drive mechanism and serves as an input element that can be adjusted by the user in order to change and set parameters in at least one predefined mode of the medication pen.

However, the constructions shown in U.S. Pat. No. 6,585, 698 B1 or in similar documents concerning medication pens, and which permit the input of parameters, do not generally solve the problems mentioned above. Thus, the amount of information to be shown on the display of such medication pens is usually not comparable to the complex and extensive information of an analysis device. Moreover, the menu control of such medication pens is not generally comparable to the complex menu control of analysis devices, since such menu controls are mostly limited only to the selection of a dose that is to be provided. Moreover, if several menu levels are to be managed, the described medication pens still require complex guiding through these menu levels, such that the above-described problems of known analysis devices are still present.

The present invention provides analysis devices that avoid the disadvantages of known analysis devices. In particular, the analysis device is intended to permit a user-friendly menu control while at the same time being technically uncomplicated. Advantageous developments of the invention, which can be implemented singly or in combination, are set forth in the dependent claims.

The invention relates to an analysis device for detecting an analyte in a liquid sample. The detection can be done qualitatively and/or quantitatively. As regards the possible analytes to be detected and/or as regards the possible forms of the liquid sample, the possible detection methods and/or the possible use of certain test elements, reference can be made, for example, to the above description of the prior art. The analysis device can be designed in particular as a portable hand-held device and so as to be easily carried around by a user, for example in a pocket of an article of clothing. In the text below, the analysis device is described in particular as an analysis device for detecting glucose in a bodily fluid, in particular for detecting blood glucose. However, other embodiments are also possible in principle as alternatives to this preferred embodiment.

The analysis device comprises at least one control element which, for example, can be configured in accordance with the above description of known control elements. The control element can in particular comprise one or more data processors which, for example, can use software technology. The control element is configured to provide a function menu with at least two menu items. A function menu is understood as a control means based at least partially on software and allowing a user to interact with the analysis device. Reference can be made, for example, to the above-described examples of such function menus. By way of this function menu, for example, control commands can be input, measurements initiated, measurement results called up, for example current measurement results and/or stored measurement results, stored data can be managed, data can be output acoustically, optically, haptically or electronically, an evaluation of measurement results can be initiated, certain values (parameters, variables) can be adjusted, for example time, date, user or the like, or combinations of said actions and/or of other actions can be performed. Various other configurations are possible.

The function menu has at least two menu items, preferably three, four or more menu items. A menu item is understood in each case as a defined mode of interaction between the analysis device and the user. Thus, each menu item can allow the user to input different types of commands and/or information, or each menu item can make different types of information available to the user. Such a menu item can also be divided into subsidiary menu items, such that one or more menu levels can be provided in each menu item. In this case, for example, the function menu with its menu items can be configured completely or partially as a tree structure.

The analysis device further comprises at least one adjustable selector element, in particular at least one mechanically adjustable selector element. A selector element is to be understood as an element which, under the action of a user, in particular a manual action, for example a turning and/or sliding, can be positioned and/or oriented in at least two different positions and/or orientations, preferably in three, four or more different positions and/or orientations. Steplessly adjustable selector elements can be used, but it is preferable to use non-stepless selector elements, that is to say selector elements that engage in a perceptible manner in a defined position and/or orientation.

The selector element is configured to remain in the adjusted selection position after being adjusted. This means that the adjusted selection position, i.e. the adjusted position and/or orientation, is at least approximately maintained without any further action from outside, for example by a user. Here, "at least approximately" is preferably to be understood as the selector element remaining exactly in the adjusted selection position. In principle, however, it can be understood as including slight deviations from the originally adjusted selection position, for example caused by spring forces or, for example, in the form of a jump to a next predefined selection position, for example if the selection element is not steplessly adjustable and the selection position adjusted by the user does not correspond exactly to the possible selection positions. Overall, the selector element is thus unlike the keys or press-buttons normally used for menu control, for example of the kind used in conventional blood glucose meters for menu control. The adjusted selection position, i.e. the adjusted position and/or orientation, can in particular be made visible from outside to an observer looking at the analysis device. This visible adjusted selection position can therefore itself serve as an indicator to the user, for example without the help of additional indicators such as electronic display means.

The selector element should be able to be adjusted by a user to at least two, preferably three, four or more different selection positions. A selection position can be understood as an orientation and/or positioning of the selector element. For example, these can be defined rotation angle positions of a rotary button and/or defined slide positions of a slide. As has been stated above, these selection positions can be perceptible by touch, such that a user recognizes that a selection position is reached.

The control is to be configured to select a menu item corresponding to the adjusted selection position. For example, a specific selection position can be predefined for one menu item, for several menu items or for all the menu items of the above-described function menu. The selector element thus allows a user, preferably without provision of complex software menu control, to jump directly to defined menu items of the function menu, without having to work through a complicated software menu. The menu items could thus be the final menu items in a tree structure. Alternatively or in addition, however, one menu item, several menu items or all the menu items can also be divided into subsidiary menu items which, for example, can be reached additionally by a software menu control or, alternatively or in addition, by one or more further selector elements of the described kind.

The analysis device further comprises at least one operating element. The at least one operating element can be configured completely or partially separately from the at least one selector element. Alternatively, however, the at least one operating element can also be combined completely or partially with the at least one selector element; for example, by one, two or more operating elements being arranged on a selector element configured as a rotary button. The at least one operating element can in this case also comprise one or more keys and/or other types of operating elements that return to their original position after an actuation, in contrast to the configuration of the at least one selector element.

The analysis device, in particular the control element, in particular the function menu, are to be configured in such a way that, by means of this operating element, at least one parameter in the menu item selected by the adjusted selection position can be influenced by the user. A parameter is to be understood here as any type of information and/or any type of command that is to be transmitted by the user to the analysis device, in particular the control element, in particular the function menu. For example, this at least one parameter, and the information contained in it, can be a numerical value; for example, a figure showing an adjustable time, date or the like. For example, if a certain place in a number is chosen by means of the selector element, which can likewise be understood as a defined menu item, the operating element allows this place to be increased and/or lowered in its numerical value for example in a simple way by means of increase keys and/or decrease keys. Alternatively or in addition, for example for transmitting control commands, the menu item can also comprise a selection of control commands which, after selection of the menu item by means of the selector element, can likewise be easily selected for example by means of selector keys of the operating element. To this extent, the term parameter is to be interpreted broadly here.

The menu control can be configured in such a way that only one of the provided and selectable menu items, some of these menu items or all of these menu items require and/or permit the influencing of one or more parameters. Accordingly, this influencing of the at least one parameter by the at least one operating element can be possible in one, several or all of the menu items, and this is intended to be included within the context of the present invention.

The operating element can be configured differently and can comprise one or more function keys and/or other kinds of input elements which permit a simple interaction with the analysis device and which are preferably multifunctional. Preferably, no more than three operating elements are provided; for example, one operating element for increasing a parameter and/or for advancing one step in a selection, one operating element for decreasing a parameter and/or for going back one step in a selection, and one operating element for an input, a confirmation or the like. Various configurations are conceivable, and various possible illustrative embodiments are described in more detail below.

The configuration of the analysis device according to the invention, with the selector element making it possible to jump directly to predefined menu items, solves the above-described problem of simplifying the menu control while at the same time ensuring a simple design of the analysis device. Thus, targeted menu control is made easier for the user, since the user is able, for example, to select a defined menu item directly using the selector element, for example a mechanically adjustable button. Thus, depending on the position of the button, it is possible to directly control a defined menu item and, therefore, a menu level.

These advantages can be further enhanced by virtue of the fact that the housing has, for example, a marking and/or inscription that explains the menu control directly, and preferably independently of an electrical functionality of the analysis device. This inscription can, for example, list the respective menu items and permit operation that is self-explanatory to a user. As soon as the selector element, for example the button, is positioned according to the listed menu item, this menu item and/or the menu level can be directly controlled and data can then be correspondingly input and/or selected accordingly via the at least one operating element.

It is particularly preferable if the analysis device has at least one housing. A marking visible to the user can be provided on this housing; for example, a marking that is optically perceivable and/or is perceivable by touch. The selector element can then be adjusted in position and/or orientation relative to the marking. The marking therefore allows the user to identify the adjusted selection position. Alternatively or in addition to a marking on the housing, a corresponding marking can also be provided on the selector element. From the relative position of these markings, the user can then identify the adjusted selection position.

The marking and the operating element can also be at least partially combined. For example, the operating element can be arranged in a fixed position and/or orientation on and/or in the housing and can thus completely or partially form part of the marking. The selector element can then be positioned and/or oriented relative to this operating element. Alternatively or in addition, however, the at least one operating element can also be completely or partially integrated in the selector element itself, such that the position and/or orientation of the operating element relative to the rest of the housing changes along with a change of the adjusted selection position. In this case, the operating element can, for example, form part of a marking arranged on the selector element.

If the analysis device has a housing, this housing and/or the selector element can have at least one function marking. This function marking, which for example can completely or partially comprise the abovementioned inscription, should be configured so as to identify at least one of the menu items and/or at least a content of at least one of the menu items. The identification of the function marking can, for example, merely entail a simple designation of the menu item, for example "Display measurement results", "Adjust date", "Adjust time", or similar designations that are preferably self-explanatory to a user. Alternatively or in addition, however, the function marking can contain further information, for example a complete or partial list of the parameters that can be influenced by means of the operating element in the respective selection position or the respectively adjusted menu item. Such a display also helps guide the user. This display also reduces the number of information items which, if appropriate, are to be shown on a display, such that this display element, which can be optionally provided, can be of a very simple configuration. Moreover, a user can directly identify the parameters which can be influenced, and which would otherwise be identifiable in a menu control only on the basis of background knowledge and/or by laboriously working through the menu. Such a configuration therefore has considerable advantages both in technical terms and also in terms of user-friendliness.

As has been explained above, the selector element can be configured in different ways. It is particularly preferable if the selector element has at least one rotary switch; for example, a button, in particular a rotary button, and/or a slide switch. As has been mentioned above, such switches can be adjusted steplessly or, preferably, in a stepped manner.

It is particularly preferable in the context of the present invention if the selector element is completely or partially integrated in the housing. In this way, the selector element does not substantially affect the external appearance and therefore the maneuverability of the housing. For example, the housing can be at least in part substantially cylindrical. "Substantially cylindrical" can also mean that slight deviations from a cylinder shape are tolerated. In this cylindrical configuration, the selector element can comprise a rotary ring at least partially surrounding the housing; for example, a substantially cylindrical rotary ring which, for example, can be oriented parallel to the axis of the cylinder shape of the housing. This rotary ring can thus be part of the cylinder shape of the housing. The rotary ring can be rotated relative to the rest of the housing in order to adjust the selection position.

As has been mentioned above, the operating element can be at least partially integrated in the selector element and/or in the rest of the housing. Preferably, no more than three operating elements are provided, since the possibility of direct selection of menu items by the selector element can ensure a simple menu control. In this way, costs incurred by additional operating elements can be avoided, while at the same time ensuring simple menu control by the at least one selector element, which can preferably be operated independently of the operation of the operating element.

The analysis device can further comprise at least one indicator element for displaying at least one variable item of information. Such an indicator element, in particular a display, can be of a simple configuration since the menu control can be effected substantially by the selector element and if appropriate by a marking and/or inscription. The number and variety of the items of information to be displayed can thus be reduced to a minimum.

This possibility of the indicator element having a simple configuration permits the use, for example, of one or more segmented displays. The indicator element can accordingly comprise at least one segmented display; for example, a seven-segment display. The advantages of such segmented displays have already been mentioned in the introduction and lie particularly in the readability, the inexpensive configuration of possible drive circuits, the compact format and the low energy requirement.

The indicator element can, for example, be completely or partially integrated in a lid of a housing of the analysis device. In the case of a cylindrical configuration of the housing, this lid can, for example, comprise a cylindrical lid of the analysis device. The lid can also be designed such that it can be flipped up and/or pivoted up in order to free at least one internal element of the analysis device. For example, the lid can be flipped up or pivoted up in order to free an application position for the liquid sample and/or a test element. In this way, the test elements and/or the application position can be protected in the interior of the housing of the analysis device and can be exposed only when the lid has been flipped up and/or pivoted up. The combination of the indicator element and of the lid that can be pivoted up and/or flipped up provides an additional saving in space.

Alternatively or in addition, the lid can also be completely or partially rotatable. In this way, for example, the selector element can be completely or partially integrated in the rotatable lid. For example, the selector element can in this case comprise a rotary switch, which can be actuated by rotation of the lid.

In addition to the elements mentioned, the analysis device can comprise further functions and/or elements. For example, in addition to the above-described qualitative and/or quantitative detection of the at least one analyte in the sample, a further medical function can be provided; for example, a sample-collecting function. For this purpose, the analysis device can, for example, comprise a sample-collecting element, which is designed to puncture an area of skin of a user. Such sample-collecting elements, which generate a sample of blood and/or another sample of bodily fluid by means of a substantially painless puncturing and/or piercing of the skin, for example in the area of a finger pad and/or of an ear lobe of a patient, are also often referred to as lancing devices. They generally contain one or more lance elements by means of which the perforation of the skin area is ensured. The sample-collecting element can be reversibly uncoupled from the rest of the analysis device and used separately. In the coupled state, the sample-collecting element and the rest of the analysis device then form one unit, which is simple and easy to transport. In the uncoupled state, the sample-collecting element can then be handled separately; for example, in order to generate a liquid sample. Alternatively, however, sample-collecting elements integrated permanently in the rest of the analysis device are also possible.

Further areas of applicability will become apparent from the description provided herein. The description and specific examples in this summary are intended for purposes of illustration only and are not intended to limit the scope of the present disclosure.

DRAWINGS

Further details and features of the invention are set forth in the following description of preferred illustrative embodiments in conjunction with the dependent claims. The respective features can be implemented singly, or several of them in combination with one another. The invention is not limited to the illustrative embodiments. The illustrative embodiments are depicted schematically in the figures. The same reference signs in the individual figures designate identical elements or designate elements that have an identical function or that correspond in terms of their functions.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom.

Figure 1:
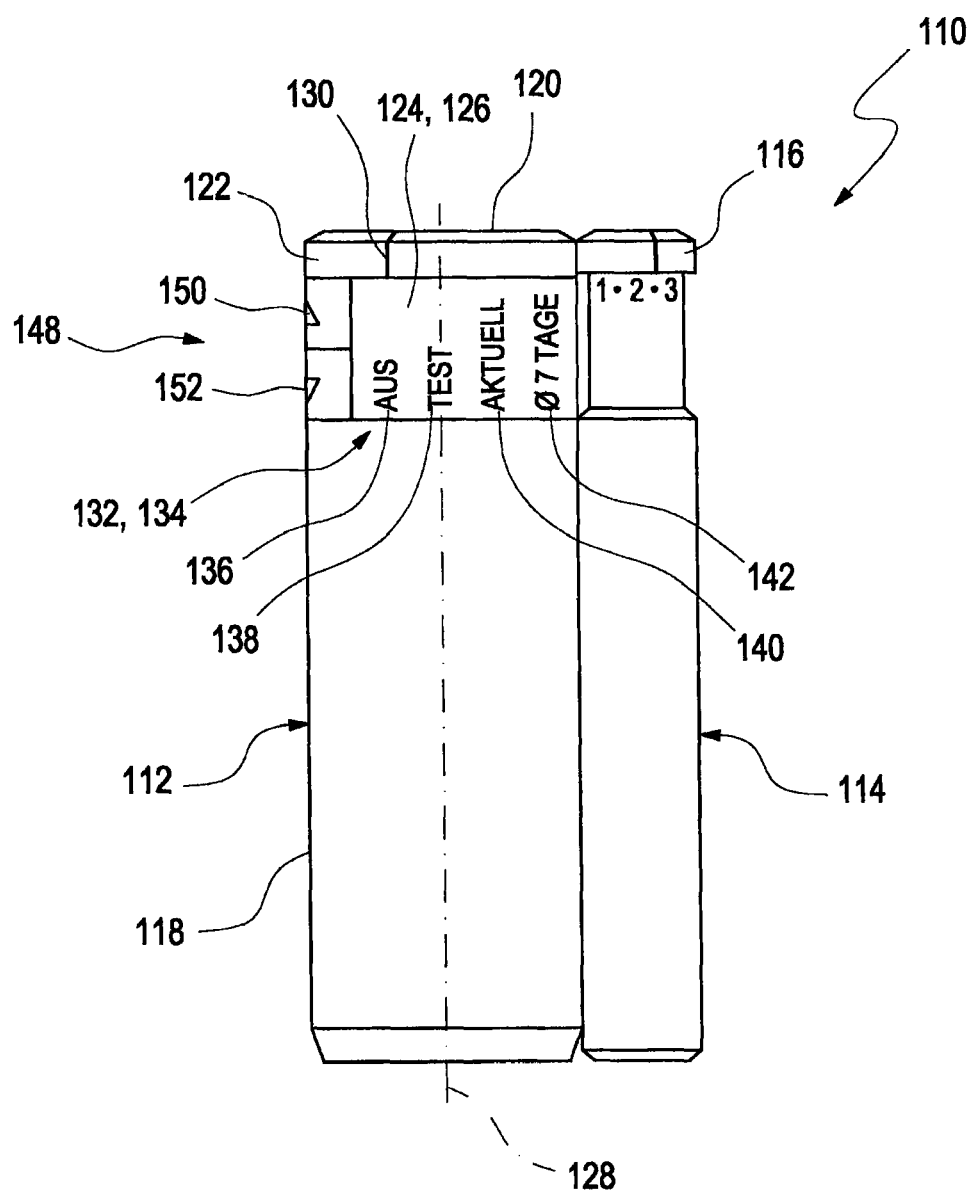
FIG. 1 shows a side view of a first illustrative embodiment of an analysis device according to the invention.

A first illustrative embodiment of an analysis device 110 according to the invention is shown in FIG. 1. This analysis device 110 can, for example, be designed as an analysis device for blood glucose determination and can determine a blood glucose concentration by means of one or more test elements. The test elements and a corresponding means for interaction of the analysis device 110 with the test elements are not shown in FIG. 1. For example, corresponding openings can be provided on a top face and/or bottom face of the analysis device 110 according to FIG. 1. Alternatively, or in addition, the analysis device 110 can also be opened at one or more places in order to permit the application of a blood sample and/or the introduction of a test element or the release of an application position of a test element. In this connection, reference is made by way of example to the illustrative embodiment described below according to FIG. 7.

The analysis device 110 is in this case designed in two parts and comprises a measuring device 112, which provides the actual functionality of the detection of the analyte. Moreover, the analysis device 110 comprises a sample-collecting element 114; for example, a lancing device. This sample-collecting element 114 is also shown only symbolically in FIG. 1 and can be designed, for example, such that a depth of penetration of a lance can be set by means of an adjustment button 116. The sample-collecting element 114 can be coupled, preferably reversibly, to the measuring device 112 by means of coupling elements not shown in detail in FIG. 1. For this purpose, hooks, rails, bayonet catches or similar coupling elements can be provided. In this way, the sample-collecting element 114 can be uncoupled reversibly from the measuring device 112 and operate independently of the measuring device 112.

In the illustrative embodiment shown, the analysis device 110 or measuring device 112 comprises a housing 118 which, for example, can have a substantially cylindrical shape. The corresponding function elements of the analysis device 110 and of the measuring device 112 can be arranged in this housing. The housing 118 can, for example, be made of plastic, metal or other materials.

Figure 2:
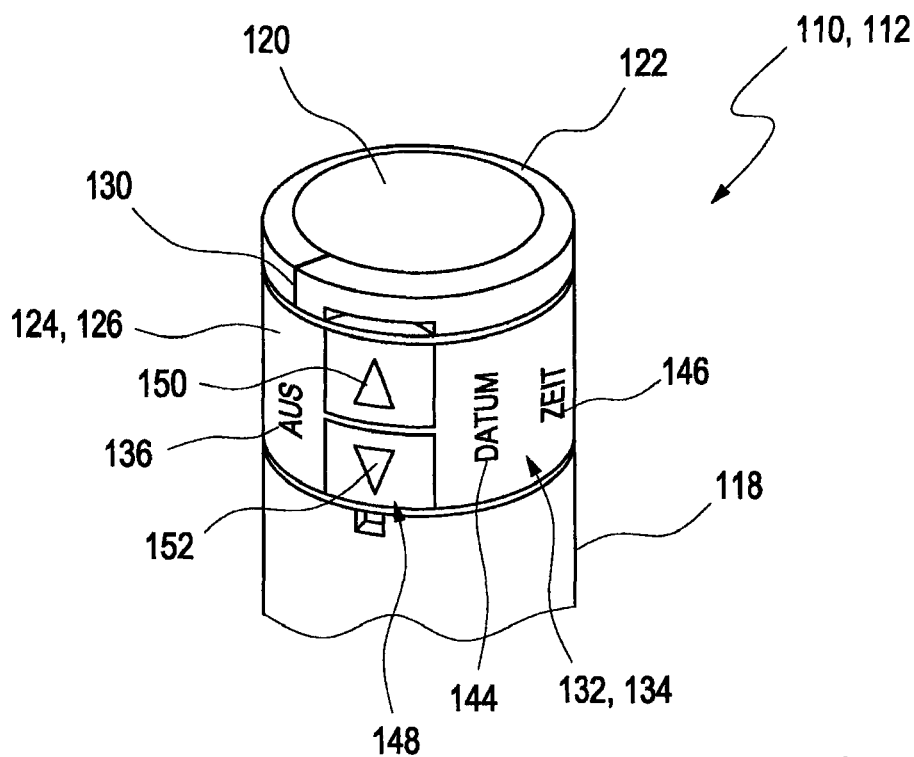
FIG. 2 shows a detail of a selector element and of the operating elements of the analysis device according to FIG. 1.
Figure 3:
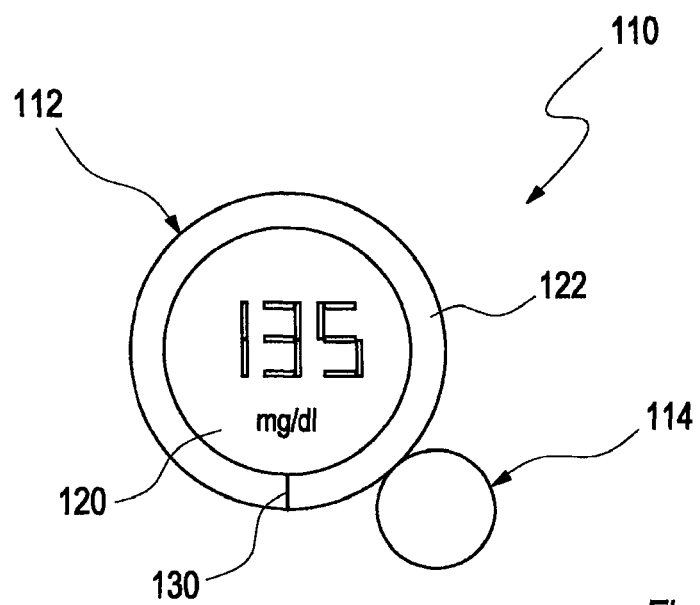
FIG. 3 shows a plan view of a lid of the analysis device according to FIG. 3, said lid containing a display.

At the upper end of the housing 118 there is an indicator element 120, which can be seen in greater detail in FIGS. 2 and 3 for example. This indicator element 120 can, for example, comprise a segmented display, as can be seen from the view according to FIG. 3 for example. The indicator element 120 can be round, for example, and can be arranged in a lid 122 of the housing 118. As is explained below, this lid 122 can also be designed as a lid 122 that can be flipped up and/or pivoted up.

The measuring device 112 in the illustrative embodiment shown in FIG. 1 also comprises a selector element 124, which is here designed in the form of a cylindrical rotary ring 126. This rotary ring can be rotated, for example within certain limits, around an axis 128 of the measuring device 112, while the rest of the housing 118 remains stationary. In this way, by means of the position of rotation of the rotary ring 126, it is possible to adopt one of several selection positions, defined by the rotation angle setting of the rotary ring 126 relative to the rest of the housing 118. The actual selection position adopted can be discerned, for example, by means of a marking 130 on the housing 118, for example on the lid 122. Alternatively, or in addition, further markings 130 can be provided on the rotary ring 126.

In the illustrative embodiment shown, the rotary ring 126 of the selector element 124 further comprises an inscription 132, which serves as a function marking 134. Alternatively, or in addition, further inscriptions 132 and/or further function markings 134 can also be provided in the rest of the housing 118 of the measuring device 112.

The inscription 132 indicates various menu items and the content thereof. The position of the inscription 132, or of the individual items of this inscription 132, relative to the marking 130 reveals the adopted selection position and, therefore, the selected menu item.

In FIG. 1, for example, four menu items can be seen, which are applied, in an axial direction of writing, on the circumference of the rotary ring 126.

Thus, a first menu item 136 is provided which is marked in FIG. 1 by "OFF" and, when this is selected, the measuring device 112 and/or the analysis device 110 can be switched to an off state or a stand-by state.

In a second menu item 138, which is designated in FIG. 1 by "TEST", it is possible, for example, for a test routine to be carried out. In a third menu item 140, which is designated in FIG. 1 by "CURRENT", it is possible, for example, for a current measured value to be displayed. In a fourth menu item 142, which is designated in FIG. 1 by "Ø 7 DAYS", it is possible, for example, to display an average value of measured results over the last 7 days.

Examples of other possible menu items can be seen in the view according to FIG. 2. Thus, a fifth menu item 144 can be provided, which is identified by "DATE" and which allows a date to be set. Moreover, a sixth menu item 146 can be provided, which is designated by "TIME" and which allows a time to be set.

Said menu items 136 to 146 only represent examples of how menu controls of the analysis device 110 can be configured. In addition to the combinations shown, numerous other combinations of said menu items and/or of other types of menu items are conceivable.

As will be evident from the description of the menu items 136 to 146, some of the menu items require one or more parameters to be influenced by a user. By way of example of such menu items in which parameters should be able to be influenced by a user, reference is made to menu items 144 and 146, in which it should be possible to set a date and/or a time; for example, a measurement date and/or a measurement time and/or a current time.

The above-listed examples of menu items 136 to 146 show that the menu items can be of very different kinds. Some of said menu items, for example menu items 136, 138, 140 or 142, can be configured in such a way that they exclusively provide information to a user, for example by being displayed on the indicator element 120. Alternatively, or in addition, menu items can also be provided which require influence by the user, in particular influence of one or more parameters. As has been explained above, these parameters can, for example, be items of information in the form of data, variables or the like that are to be input, or also control commands.

As an example of such menu items that are intended to at least permit the influence of one or more parameters, mention is made of menu items 144 and 146 according to FIG. 2, that is to say the setting of date and/or time. A prompt to carry out a measurement, a prompt to display certain information, a prompt to carry out certain evaluations or the like can be included in this category of menu items that are intended to permit the influencing of at least one parameter.

In order to influence the at least one parameter, operating elements 148 are provided in the illustrative embodiment shown in FIGS. 1 and 2. These operating elements in the illustrative embodiment shown are integrated in the selector element 124 and comprise an advance key 150 and a return key 152. Using the advance key 150, which is marked in FIGS. 1 and 2 by an upwardly directed arrow, it is possible, for example, to increase parameter values or to go one step forward in a function menu. By means of the return key 152 marked by a downwardly directed arrow, it is possible, for example, to reduce values or to go back steps in a selection menu. However, the illustrated configuration of the operating elements 148 is only one of many possible configurations, wherein it is possible to provide more keys than the two keys 150, 152, wherein another kind of marking can also be chosen, or wherein an entirely different configuration can be chosen. Moreover, the operating elements 148 do not have to be securely integrated in the display element 120, such that they also rotate upon rotation of the rotary ring 126 for example, and instead it is also possible, alternatively or in addition, to choose a completely or partially fixed arrangement of the operating elements 148. Various other configurations are shown below.

Figure 4:
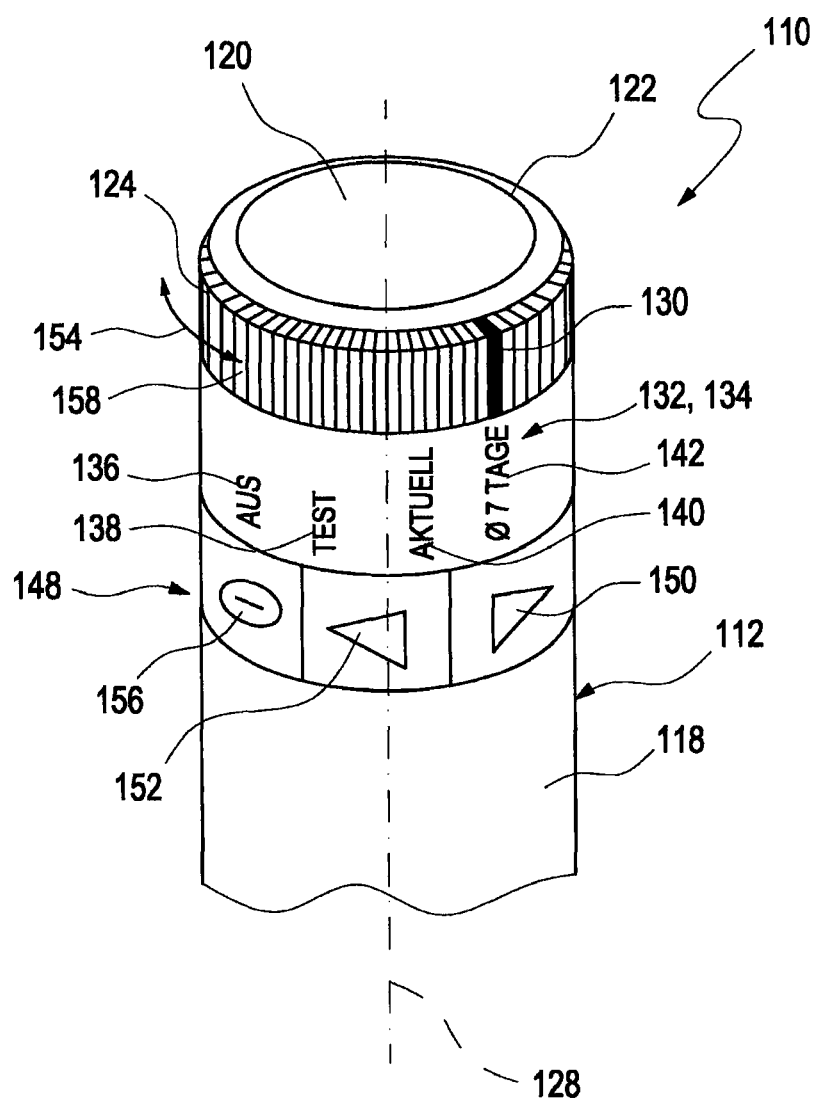
FIG. 4 shows another illustrative embodiment of an analysis device according to the invention in a view analogous to FIG. 2.

FIG. 4, in a view analogous to FIG. 2, shows an alternative illustrative embodiment of an analysis device 110. Only a measuring device 112 is shown here. However, the analysis device 110 can once again optionally have, analogously to FIG. 1, a sample-collecting element 114 (not shown in FIG. 4).

In the illustrative embodiment according to FIG. 4, the device 112 is once again cylindrical, such that, for the configuration of many of the elements of this measuring device 112, reference can be made, for example, to the above description of FIGS. 1 to 3.

In FIGS. 1 to 3, it was assumed that the selector element 124 is formed by the rotary ring 126. As an alternative to this solution, however, a rotation of the lid 122 relative to the rest of the housing 118 could also take place, such that the selector element 124 would be at least partially identical to the lid 122. In this case, for example, the inscription 132 and/or the operating elements 148 would be completely or partially fixed in position relative to the rest of the housing 118, whereas the lid 122 would be rotated about the axis 128. The illustrative embodiment shown in FIG. 4 is configured in this way. It will be noted, however, that in the illustrative embodiment shown in the figure it would also be alternatively possible for the lid 122 to be fixed in position relative to the rest of the housing 118, whereas a rotary ring 126 could once again be arranged under the lid 122, in the area of the inscription 132. However, as is indicated by reference number 154, FIG. 4 shows a rotation of the lid 122 relative to the rest of the housing 118, for selecting a defined selection position.

As has been mentioned above, the inscription 132 functioning as function marking 134 can therefore be arranged completely or partially on the selector element 124 and/or completely or partially on another fixed part of the housing 118. The inscription 132, which for example can once again be configured analogously to the configuration in FIGS. 1 and 2, is only indicated symbolically in FIG. 4.

The illustrative embodiment according to FIG. 4 also differs in terms of the configuration of the operating elements 148. In the illustrative embodiment shown, these operating elements 148 are also arranged in a fixed position relative to the rest of the housing 118, which can for example also afford advantages in an electrical connection of these operating elements 148. Alternatively, however, a complete or partial arrangement of these operating elements 148 on the rotatable selector element 124, for example in the area of the lid 122, is once again also conceivable.

The operating elements 148 according to the illustrative embodiment in FIG. 4 also differ in other ways from the operating elements according to the illustrative embodiment in FIGS. 1 and 2. An advance key 150 and a return key 152 are again provided, for example with the functionalities described above. An input key 156 is also provided which, for example, can be used to confirm entries and/or to select a defined menu. However, such an input key can also be optionally integrated in the illustrative embodiment according to FIGS. 1 and 2.

In the case shown in FIG. 4, where the selector element 124 is formed completely or partially by a rotatable lid 122 in which an indicator element 120 is also integrated, the edge of this lid 122 can be made grippable, for example by corresponding gripping grooves 158, which are indicated in FIG. 4. Such gripping grooves 158 can also be provided in the illustrative embodiment according to FIGS. 1 to 3, particularly if the described variant with the rotary ring 126 is not being used there, and instead the selector element 124 is likewise formed by a rotatable lid 122. If the lid 122 is rotatable, the measuring device 112 can be configured in such a way that the indicator element 120 also rotates upon rotation of the lid 122. Alternatively, however, the indicator element 120 can also remain completely or partially fixed in position against rotation, and only a frame of the lid 122 can be rotated, which then once again forms a rotary ring 126. Various configurations are possible.

Figure 5:
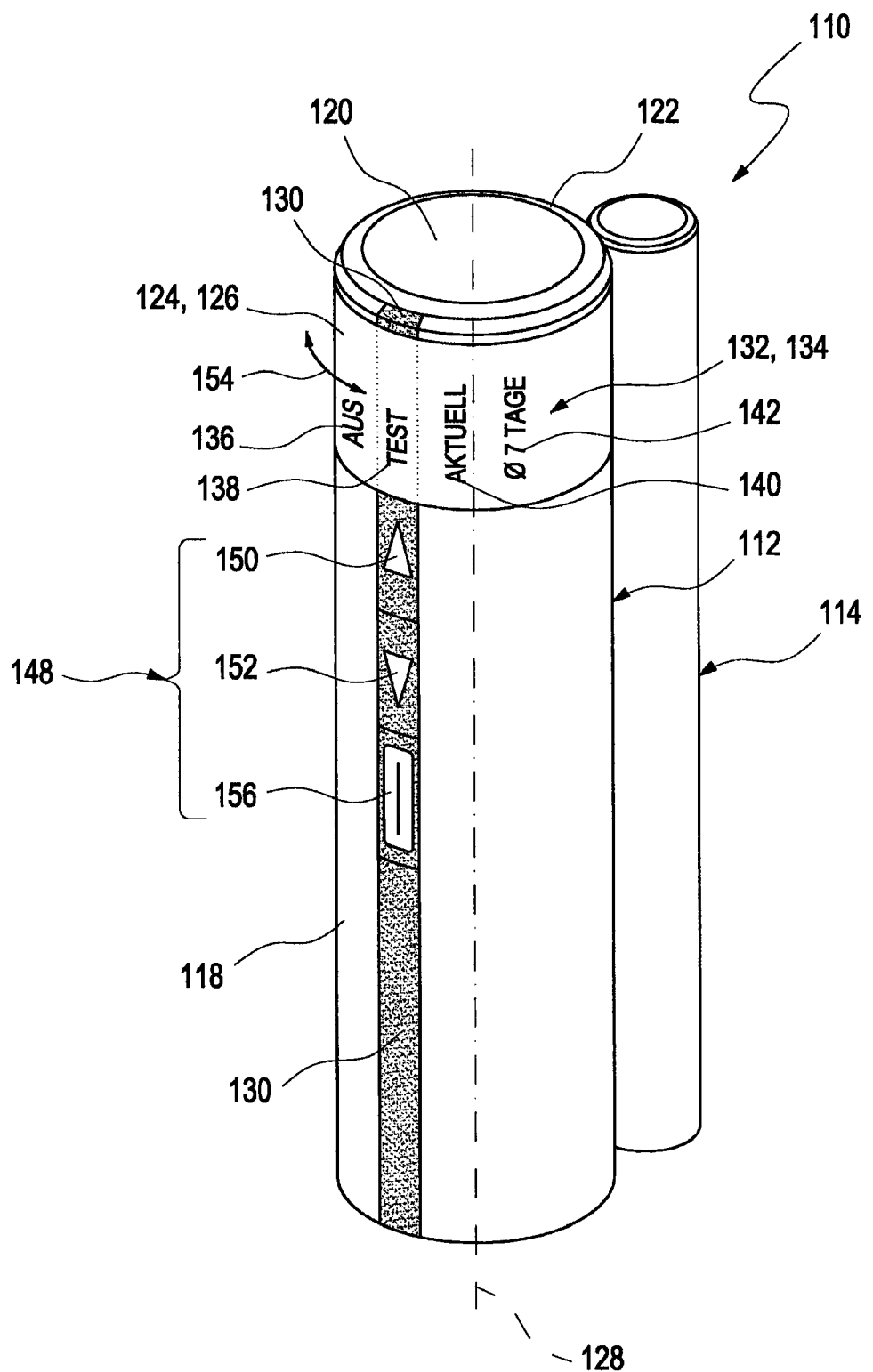
FIG. 5 shows another illustrative embodiment of an analysis device according to the invention in a view analogous to FIG. 2.

As an alternative to FIG. 1, FIG. 5 shows a perspective view of another illustrative embodiment of an analysis device 110 according to the invention with a measuring device 112 and an optional sample-collecting element 114. The sample-collecting element 114 is only indicated symbolically and can, for example, be configured analogously to the embodiment according to FIG. 1. In the illustrative embodiment according to FIG. 5, the measuring device 112 is again provided with a housing 118 which, for example, can again be substantially cylindrical. For other parts of the embodiment according to FIG. 5, reference can be made to the description of the illustrative embodiment according to FIGS. 1 to 3.

The housing 118 of the measuring device 112 once again has a circular lid 122. In this illustrative embodiment, it is assumed that the lid 122 is fixed against rotation, analogously to the above description of the illustrative embodiment in FIGS. 1 to 3. However, a rotatable configuration of the lid 122 is also possible; for example, analogously to the above description of the illustrative embodiment according to FIG. 4.

Depending on the embodiment chosen, the measuring device 112 once again has a selector element 124 in the form of a rotary ring 126, which for example can be arranged on the upper end of the housing 118, under the lid 122.

However, other arrangements of the rotary ring 126 or of the selector element 124 are also possible in principle.

Analogously to the above description of the illustrative embodiment according to FIGS. 1 to 3, the rotary ring 126 once again has an inscription 132, which serves as a function marking 134 and which, for example, can be configured analogously to the illustrative embodiment according to FIGS. 1 to 3. This inscription 132 is only shown symbolically in FIG. 5.

The housing 118 of the measuring device 112 once again has a marking 130 which, in this illustrative embodiment, is in the form of a strip that extends in the axial direction and that continues as far as the lid 122 and is interrupted only by the rotary ring 126. Depending on which of the menu items of the function marking 134 is oriented linearly with respect to this strip-shaped marking 130 by suitable rotation 154, a defined menu item of a function menu is selected.

The measuring device 112 once again has operating elements 148. FIG. 5 shows an optional embodiment in which these operating elements 148 are integrated completely or partially in the marking 130, such that it is immediately clear in an intuitive way that these operating elements relate to the respectively selected menu item. The operating elements 148 can once again comprise, for example, an advance key 150, a return key 152 and an input key 156. However, other configurations are also possible, for example a configuration with two keys 150, 152, for example FIG. 2.

Figure 6:
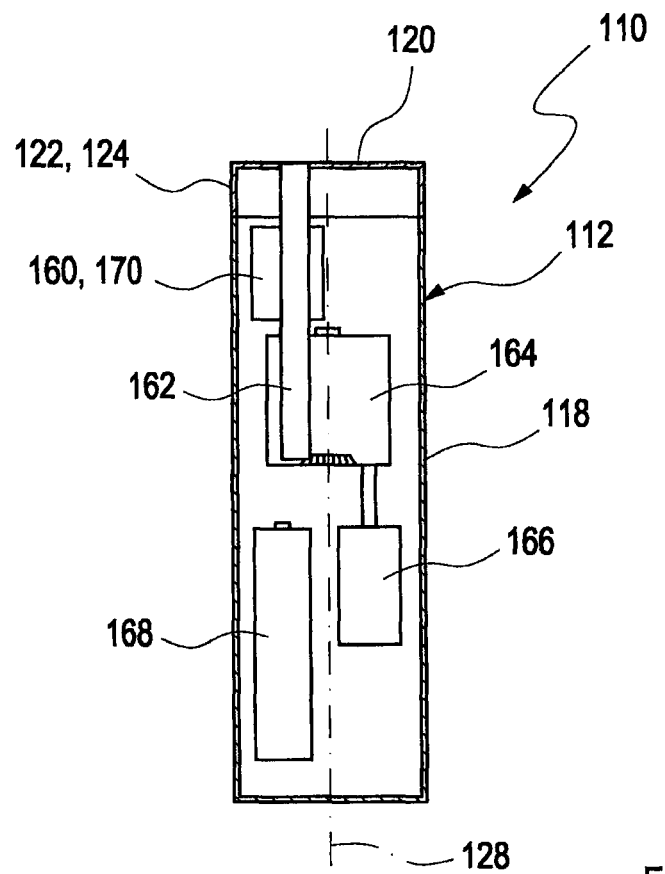
FIG. 6 shows a sectional view of a possible illustrative embodiment of an analysis device.

FIG. 6 shows a sectional view of a possible internal structure of a measuring device 112; for example, according to one or more of the illustrative embodiments according to FIGS. 1 to 5. It will be noted that another structure is also possible. For other parts of the embodiment, reference can accordingly be made to the description of the above figures. A measuring device 112 is shown only by way of example, in which the selector element 124 is completely or partially integrated in the lid 122. Alternatively, however, the embodiments with a rotary ring are also possible, for example according to FIG. 1 or according to FIG. 5. The operating elements 148 are not shown in FIG. 6.

In the housing 118 of the measuring device 112 shown in FIG. 6, which housing 118 is for example once again cylindrical in shape, various structural elements are arranged along the axis 128 of the measuring device 112. For example, the measuring device 112 can comprise a measuring unit 160 which, in this illustrative embodiment, is arranged under the lid 122. However, another arrangement is also possible in principle, for example at a lower end of the housing 118 remote from the lid 122.

The measuring unit 160 is optionally configured as a measuring unit that is based on the use of one or more test elements 162. Embodiments are possible in which these test elements 162 can be introduced into the measuring device 112 from the outside. FIG. 6 shows an option in which several test elements 162 are arranged in a magazine, for example a cylindrical drum magazine, in the interior of the housing 118 and can be made available in succession to the measuring unit 160. Various other configurations are also possible; for example, the use of stack magazines, tape magazines, test tapes or the like. The drum magazine is indicated in FIG. 6 by reference number 164.

In order to provide test elements 162, the drum magazine 164 can optionally rotate about the axis 128 or about an axis parallel to this axis 128. In order to ensure this rotation, the measuring device 112 comprises a drive 166 which, for example, can comprise one or more motors and, if appropriate, a suitable gearing and which can effect a rotation of the drum magazine 164.

Finally, the measuring device 112 comprises one or more energy storage means 168; for example, one or more batteries and/or accumulators. These can supply electrical energy, for example to the measuring unit 160 and/or to the drive 166.

The measuring device 112 further comprises one or more control elements 170. This control element 170 can, for example, be completely or partially combined with the measuring unit 160. Alternatively or in addition, however, it is also possible for a control element 170 to be configured separately from the measuring unit 160; for example, a decentralized control element. Such a control element 170 can, for example, be configured to perform the menu control explained above and, accordingly, to carry out a control of the measurements, data storage and data administration, data evaluation or similar. Various configurations are conceivable.

Figure 7:
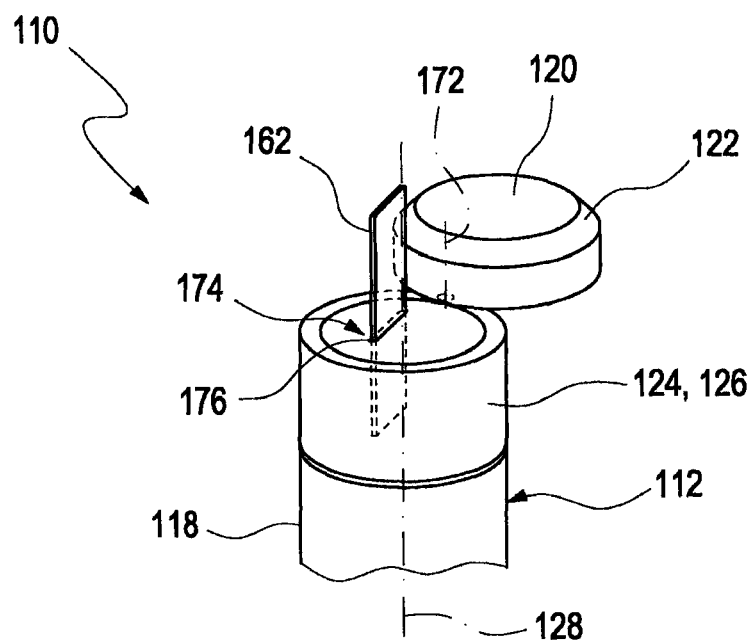
FIG. 7 shows a schematic view of a lid of an analysis device according to the invention being swiveled open.

FIG. 7 finally shows an illustrative embodiment of an analysis device 110 with a measuring device 112 which comprises a pivotable lid 122. The measuring device 112 can be configured analogously to the embodiments described above. In the following it is assumed that the analysis device is configured analogously to the illustrative embodiment according to FIGS. 1 to 3, where a selector element 124 in the form of a rotary ring 126 is provided.

Alternatively or in addition, however, the lid 122 can once again also be configured completely or partially as a rotatable selector element 124. For further possible configurations of the measuring device 112, reference can accordingly be made to the above description. In the illustrative embodiment shown in FIG. 7, the lid 122, which can once again comprise the indicator element 120 for example, is mounted so as to be rotatable about an axis of rotation 172, such that the lid 122 can deflect from the orientation concentric to the axis 128. In this pivoted state shown in FIG. 7, an application position, indicated symbolically by reference number 174, in the interior of the measuring device 112 is freed, in which a test strip 162, for example, can be pushed out of a dispensing slit 176 to such an extent that a blood sample and/or another liquid sample can be applied thereto. A measurement can also optionally take place in this position. After the measurement, the test element 162 can be accommodated again in the magazine, for example the drum magazine 164, or can be disposed of in another way, for example ejected.

The measuring device 112 can be configured such that the selector element 124 can be operated even while the lid 122 is being opened or when said lid 122 is in the opened position. Alternatively, however, it can be configured such that such an operation is possible only in the closed state. Various embodiments are conceivable.

LIST OF REFERENCE NUMERALS

110 analysis device
112 measuring device
114 sample-collecting element
116 adjustment button
118 housing
120 indicator element
122 lid
124 selector element
126 rotary ring
128 axis 130 marking
132 inscription
134 function marking
136 first menu item
138 second menu item
140 third menu item
142 fourth menu item
144 fifth menu item
146 sixth menu item
148 operating elements
150 advance key
152 return key
154 rotation
156 input key
158 gripping grooves
160 measuring unit
162 test element
164 drum magazine
166 drive
168 energy storage means
170 control element
172 rotation axis
174 application position
176 dispensing slit

What is claimed is:

1. An analysis device for detecting an analyte in a liquid sample, in particular for detecting glucose in a bodily fluid, comprising:
   at least one controller comprising one or more data processors configured to provide a function menu with at least three menu items;
   at least one mechanically adjustable selector element configured to be adjusted by a user to at least three different selection positions and remain in an adjusted selection position after being adjusted, wherein each selection position corresponds to at least one of the menu items for operation with a function of the analysis device; and
   a housing, wherein the housing and/or the selector element has at least one function marking with at least one inscription of the selector element and/or of the housing, wherein the function marking designates at least one of the menu items and/or at least a content of at least one of the menu items, wherein the inscription is designed to explain a menu control directly and independently of an electrical functionality of the analysis device,
   wherein the controller is configured to select a menu item corresponding to the adjusted selection position of the selector element, wherein movement of the selector element allows the user to jump directly to predefined menu items, wherein a certain menu item can be selected by a user directly via movement of the selector element, wherein the analysis device further comprises at least one operating element, wherein at least one parameter in the selected menu item can be influenced by the user via the operating element.

2. The analysis device according to claim 1, wherein the housing has a marking perceptible to the user, wherein the selector element can be adjusted in one or both of position and orientation relative to the marking.

3. The analysis device according to claim 2, wherein the operating element and the marking are at least partially combined.

4. The analysis device according to claim 1, wherein the function marking is configured to at least partially indicate parameters, which can be influenced by means of the operating element, of the menu item selected by the selection position.

5. The analysis device according to claim 1, wherein the selector element comprises at least one rotary switch and/or one slide switch.

6. The analysis device according to claim 1, wherein the housing is at least in part substantially cylindrical, wherein the selector element comprises at least one rotary ring at least partially surrounding the housing, wherein the rotary ring can be rotated relative to the rest of the housing in order to adjust the selection position.

7. The analysis device according to claim 1, wherein the analysis device comprises a rotatable lid, wherein the selector element is completely or partially integrated in the rotatable lid.

8. The analysis device according to claim 1, wherein the operating element is at least partially integrated in the selector element.

9. The analysis device according to claim 1, wherein no more than three operating elements are provided.

10. The analysis device according to claim 1, further comprising an indicator element for displaying at least one variable item of information.

11. The analysis device according to claim 10, wherein the indicator element comprises at least one segmented display.

12. The analysis device according to claim 10, wherein the indicator element is at least partially integrated in a lid of the housing of the analysis device, particularly a lid of a cylindrical housing of the analysis device.

13. The analysis device according to claim 1, wherein the analysis device comprises a lid, wherein the lid is designed such that it can be one or both of pivoted up and flipped up, in order to free at least one internal element of the analysis device.

14. The analysis device according to claim 13, wherein the at least one internal element of the analysis device is selected from the group consisting of an application position on which the liquid sample can be placed, a test element, or a combination thereof.

15. The analysis device according to claim 1, further comprising at least one sample-collecting element, which is operable to puncture an area of skin of a user.

16. The analysis device according to claim 15, wherein the sample-collecting element can be reversibly uncoupled from the rest of the analysis device and used separately.

17. An analysis device for detecting an analyte in a liquid sample, in particular for detecting glucose in a bodily fluid, comprising:
   at least one controller configured to provide a function menu with at least three menu items;
   at least one mechanically adjustable selector element configured to be adjusted by a user to at least three different selection positions and remain in an adjusted selection position after being adjusted, wherein each selection position corresponds to at least one of the menu items for operation with a function of the analysis device; and
   a housing having at least one function marking with at least one inscription perceptible to the user, wherein the function marking designates at least one of the menu items and/or at least a content of at least one of the menu items, wherein the inscription is designed to explain a menu control directly and independently of an electrical functionality of the analysis device and the selector element can be adjusted in one or both of position and orientation relative to the function marking, wherein the controller is configured to select a menu item corresponding to the adjusted selection position of the selector element, wherein movement of the selector element allows the user to jump directly to predefined menu items, wherein a certain menu item can be selected by a user directly via movement of the selector element, wherein the analysis device further comprises at least one operating element, wherein at least one parameter in the selected menu item can be influenced by the user via the operating element.

18. The analysis device according to claim 1, wherein the controller is configured to perform a function associated with the menu item corresponding to the adjusted selection position of the selector element.

19. The analysis device according to claim 1, wherein the housing includes at least one inscription of the menu items and the selector element comprises a rotary ring at least partially surrounding the housing, wherein the rotary ring can be rotated relative to the rest of the housing in order to adjust the selection position relative to a menu item.

* * * * *